US006187803B1

(12) United States Patent
Yoshii et al.

(10) Patent No.: US 6,187,803 B1
(45) Date of Patent: *Feb. 13, 2001

(54) DRUG PREPARATION FOR ORAL ADMINISTRATION

(75) Inventors: Haruo Yoshii; Yuriko Yamazaki, both of Katoh-gun (JP)

(73) Assignee: Nippon Zoki Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/013,202

(22) Filed: Jan. 26, 1998

(30) Foreign Application Priority Data

Jan. 30, 1997 (JP) .................................................... 9-031311

(51) Int. Cl.⁷ ........................... A61K 31/415; A61K 38/21
(52) U.S. Cl. ............................ 514/400; 424/85.8; 424/86
(58) Field of Search ...................... 424/85.8, 86; 514/400

(56) References Cited

U.S. PATENT DOCUMENTS

| 3,873,697 | 3/1975 | Filipp et al. | 424/177 |
| 4,704,273 | 11/1987 | McMichael | 424/85 |
| 4,705,685 | * 11/1987 | McMichael | 424/89 |
| 4,705,687 | 11/1987 | Lau | 424/95 |
| 4,812,449 | 3/1989 | Rideout | 514/183 |
| 5,112,738 | 5/1992 | Buckler et al. | 436/822 |
| 5,354,848 | 10/1994 | Faligiani et al. | 530/395 |
| 5,622,970 | 4/1997 | Armistead et al. | 514/315 |
| 5,639,758 | 6/1997 | Sharpe et al. | 514/278 |
| 5,780,026 | 7/1998 | Yoshii et al. | 424/130.1 |

FOREIGN PATENT DOCUMENTS

| 0 646 376 A1 | * 4/1995 | (EP) | A61K/38/16 |
| 0 758 656 A2 | 2/1997 | (EP) | A61K/39/395 |

OTHER PUBLICATIONS

Peacock, Jr., E. E., *Wound Repair* Third Edition, W. B. Saunders Co., 1984, pp. 96–97.
Fahey et al., "Status of immune–based therapies in HIV infection and AIDS," *Clin. exp. Immunol.* (1992) 88, 1–5.
*Fundamental Immunology* Third Edition, W. E. Paul, Editor, Raven Press, 1993, pp. 1354–1369.
Kaneko, et al., "Role of Interleukin–5 in Local Accumulation of Eosinophils in Mouse Allergic Peritonitis," *Int. Arch Allergy Appl Immunol.*, 1991; 96: 41–45.
Kaplan, A.P., *Allergy*, second edition, 1977, pp. 148–178, 260–261, 426–427, 439–440, 456–457, 482–483, 554, 597–598, 861–875.
Roitt, I. et al, "Hypersensitivity—Type IV", *Immunology*, 2nd ed., 1989, pp. 22.1–22.10.

Dunn, C. J., et al., "Murine Delayed–Type Hypersensitivity Granuloma: An Improved Model For The Identification And Evaluation Of Different Classes of Anti–Arthritic Drugs," *Int. J. Immunopharmac.*, vol. 12, No. 8, pp. 899–904, 1990.
Yu, M., et al., "Interferon–β inhibits progression of relapsing–remitting experimental autoimmune encephalomyelitis," *Journal of Neuroimmunology* 64 (1996), pp. 91–100.
Arnason, "Interferon Beta in Multiple Sclerosis," *Clinical Immunology and Immunopathology*, vol. 81, No. 1, Oct., pp. 1–11, 1996.
The Merck Index, Twelfth Edition, 1996, p. 807.
*Sigma Biochemicals Organic Compounds for Research and Diagnostic Reagents*, 1995, pp. 470–472, and 1365–1368.
Curtis, et al., *Biology*, Fifth edition, Worth Publishers (New York), 1989, pp. 835–836.
M. Naiki et al., "Neurotropin Inhibits Experimental Allergic Encephalomyelitis (EAE) in Lewis Rats", *Int. J. Immunopharmac.*, 13(2/3), 235–243 (1991).
"Drug Evaluations Annual 1995", American Medical Association, pp. 438–445 (1995).
Goodin, "The use of immunosuppressive agents in the treatment of multiple sclerosis: A critical review", *Neurology*, vol. 41, pp. 980–985 (1991).
Higashiguchi, et al., Chemical Abstracts 112:111828b, 1990.
Gertlik, et al., Chemical Abstracts 67, #5, 20482v, 1967.
Volokhovskaya, et al., Chemical Abstracts, 115:21847q, 1991.
Yoshii, et al., "Inhibitory Effect of Histamine–Added Mouse γ–Globulin On Eosinophil Accumulation Induced By Allergen in Balb/c Mice", *Japanese Journal of Allergology*, 44:567–570 (1995).
Yoshii, et al., "A New Assay System Detecting Antibody Production And Delayed–Type Hypersensitivity Responses To Trinitrophenyl Hapten In An Individual Mouse", *Int. J. Immunopharmac.*, vol. 18, No. 1, pp. 31–36, 1996.

(List continued on next page.)

*Primary Examiner*—Russell Travers
(74) *Attorney, Agent, or Firm*—Hollander Law Firm, P.L.C.

(57) ABSTRACT

A drug preparation for oral administration containing histamine-added immunoglobulin as an effective component may be used for prevention or treatment of allergic diseases such as bronchial asthma, allergic rhinitis, vasomotor rhinitis, urticaria, chronic eczema and atopic dermatitis; autoimmune diseases such as multiple sclerosis, chronic rheumatoid arthritis and systemic lupus erythematodes; various immunodeficiency syndromes; and also eosinophilia or various inflammatory diseases caused by infectious diseases, parasitic diseases, diseases of respiratory organs, autoimmune diseases, and malignant tumors. The drug preparation which can be administered orally can be taken by patients easier than an injectable preparation without loss of effectiveness. Therefore, the drug preparation for oral administration of the present invention is practical and highly useful.

20 Claims, 3 Drawing Sheets

OTHER PUBLICATIONS

Fujiwara, et al., "Sandwich enzyme immunoassay of tumor-associated antigen sialosylated Lewis using β–D–galactosidase coupled to a monoclonal antibody of IgM isotype", *Journal of Immunological Methods*, 112, pp. 77–83, 1988.

Burnham, "Polymers for delivering peptides and proteins", *Am J Hosp Pharm*, vol. 51, pp. 210–218, Jan. 15, 1994.

Wood, et al., Biochemistry A Problems Approach, 2nd edition, pp. 155–156, 1981.

Naiki, et al., 9th International Congress of Immunology, p. 183, abstract 1084, Jul. 23–29, 1995.

Atton–Chamla et al., "Premenstrual syndrome and atopy: a double–blind clincal evaluation of treatment with a gamma–globulin/histamine complex," *Pharmatherapeutica*, vol. 2, No. 7, 1980, pp. 481–486.

Tanizaki et al., "Inhibitory Effect of Histamine–Gamma Globulin Conjugate on IgE–Mediated Reactivity of Human Basophils," *Jpn. J. Allergol.* 33, (12), pp. 1025–1029, 1984.

* cited by examiner

□ : Control (Physiological saline solution, oral administration)
○ : Positive control (HG75, hypodermic injection)
● : HG75, oral administration

DRUG PREPARATION FOR ORAL ADMINISTRATION

This Application claims priority from Japanese Patent application No. 31,311/1221 filed Jun. 30, 1997

FIELD OF THE INVENTION

The present invention relates to a drug preparation for oral administration containing histamine-added immunoglobulin as an effective component.

BACKGROUND OF THE INVENTION

A complex of immunoglobulin and histamine has been known as a drug preparation, histamine-added immunoglobulin. It restores histamine fixing ability which is lowered in patients suffering from allergy and asthma. Accordingly, histamine-added immunoglobulin is used as an agent for nonspecific hyposensitizing therapy for bronchial asthma, allergic rhinitis, vasomotor rhinitis, and allergic skin diseases such as urticaria, chronic eczema, atopic dermatitis, etc. Histamine-added immunoglobulin also exhibits suppressive action to liberation of histamine. It does not exhibit side effects exhibited by antihistamines and adrenocortical hormones used as symptomatic remedies. It has therefore been widely used as a pharmaceutical agent with high safety. See pages 463 and 464 of "Drugs in Japan, Ethical Drugs," edited by Japan Pharmaceutical Information Center; published by Yakugyo Jiho Co., Ltd., Japan in October 1996.

Histamine-added immunoglobulin is administered by a hypodermic injection because it is a proteinic preparation. There has been no report of its pharmaceutical effects by oral administration.

The present inventors have conducted various tests and studies on the pharmacological activity of histamine-added immunoglobulin. As a result, they have unexpectedly found that said histamine-added immunoglobulin has the same pharmacological activity as shown by the conventional hypodermic injection even if it is administered orally whereupon the present invention has been achieved.

The present invention provides a pharmaceutical composition for oral administration containing histamine-added immunoglobulin as an active component. The composition is shelf-stable over an extended period of time and is easily administered by a patient. The histamine-added immunoglobulin may be administered orally for the treatment of allergic diseases such as bronchial asthma, allergic rhinitis, vasomotor rhinitis, urticaria, chronic eczema and atopic dermatitis; autoimmune diseases such as multiple sclerosis, chronic rheumatoid arthritis and systemic lupus erythematodes; various immunodeficiency syndromes; and also eosinophilia or various inflammatory diseases caused by infectious diseases, parasitic diseases, diseases of respiratory organs, autoimmune diseases, malignant tumor, etc.

SUMMARY OF THE INVENTION

An allergic disease, autoimmune disease, immunodeficiency syndrome, inflammatory disease, or eosinophilia may be treated by orally administering to a patient in need of such treatment an orally ingestible, pharmaceutical composition comprising a pharmaceutically effective amount of a histamine-added immunoglobulin and a pharmaceutically acceptable carrier. The pharmaceutical composition is shelf-stable for extended periods of time and is more easily administered orally than by injection. Even though the composition contains a proteinic component, its efficacy is not substantially lost even though it is administered orally and subjected to digestive action of the stomach and intestines.

The histamine-added immunoglobulin may be prepared by dissolving about 1 mg to about 200 mg, preferably about 5 mg to about 50 mg, of immunoglobulin and about 0.01 $\mu$g to about 2 $\mu$g, preferably about 0.05 $\mu$g to about 0.5 $\mu$g, of a histamine component in a suitable pharmaceutically acceptable solution. The solution of histamine-added immunoglobulin may be prepared in a dry state or the solution may be filled in vials or the like followed by freeze-drying. Additives or carriers may be added in pharmaceutically acceptable amounts with one or more binders, disintegrating agents, lubricating agents, bulking agents, moisturizing agents, buffers, preservatives, or perfumes to obtain orally ingestible pharmaceutical compositions in the form of tablets, diluted powders, granules or capsules.

Exemplary of diseases which may be treated by oral administration of the histamine-added immunoglobulin are allergic diseases such as bronchial asthma, allergic rhinitis, vasomotor rhinitis, urticaria, chronic eczema and atopic dermatitis; autoimmune diseases such as multiple sclerosis, chronic rheumatoid arritis and systemic lupus erythematodes; various immunodeficiency syndromes; and also eosinophilia or various inflammatory diseases caused by infectious diseases, parasitic diseases, diseases of respiratory organs, autoimmune diseases, and malignant tumors.

DETAILED DESCRIPTION OF THE INVENTION

Figure 1:
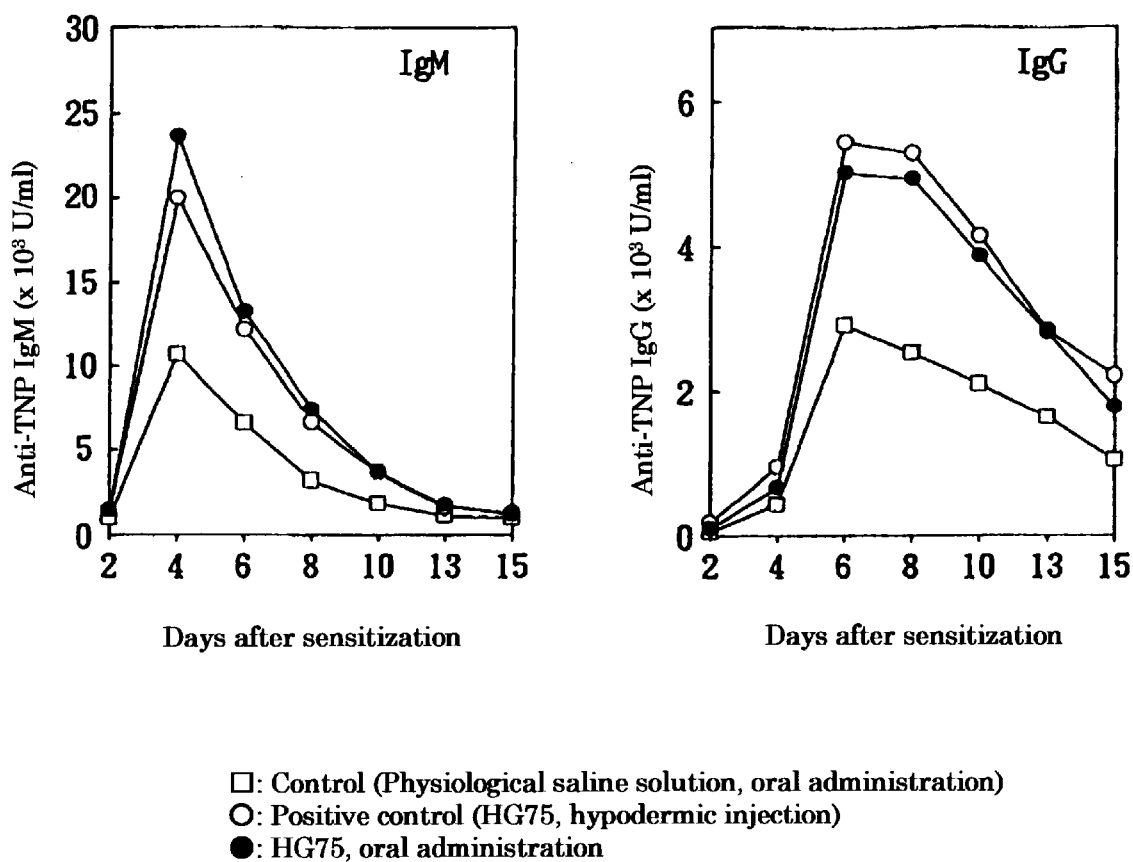
FIG. 1 is a graph showing the promoting action of a drug preparation for oral administration of the present invention on anti-TNP antibody production.

The present invention provides a drug preparation for oral administration containing histamine-added immunoglobulin as an effective component. Even though it is a proteinic preparation, it may be orally administered without substantial loss of effectiveness for restoring histamine fixing ability which is lowered in patients suffering from allergy and asthma. Accordingly, it may be administered orally by a patient, which is easier than injection, for nonspecific hyposensitizing therapy for bronchial asthma, allergic rhinitis, vasomotor rhinitis, and allergic skin diseases such as urticaria, chronic eczema, atopic dermatitis, etc. The orally administered, histamine-added immunoglobulin also exhibits suppressive action towards liberation of histamine. It does not exhibit side effects exhibited by antihistamines and adrenocortical hormones used as symptomatic remedies. In accordance with the present invention, phannaceutically effective amounts of histamine-added immunoglobulin may be orally administered to a patient for the treatment of allergic diseases such as bronchial asthma, allergic rhinitis, vasomotor rhinitis, urticaria, chronic eczema and atopic dermatitis; autoimmune diseases such as multiple sclerosis, chronic rheumatoid arthritis and systemic lupus erythematodes; various immunodeficiency syndromes; and also eosinophilia or various inflammatory diseases caused by infectious diseases, parasitic diseases, diseases of respiratory organs, autoimmune diseases, and malignant tumors.

Histamine-added immunoglobulin, which is an effective component of the drug preparation for oral administration of the present invention, can be prepared by mixing of an immunoglobulin component with a histamine component to obtain a substantially homogeneous mixture. Preferred immunoglobulin which is usable in the present invention depends upon the subject to be treated. In the case of a pharmaceutical agent which is used for treatment of a human being, it goes without saying that human immunoglobulin may be used as a material. The human immunoglobulin can be obtained from serum or placenta plasma by conventional methods. In order to secure safety as a pharmaceutical agent, the standards which are usually stipulated for plasma fraction preparations should be satisfied. For example, when human plasma which is negative to HB's antigen, HCV antibody and HIV antibody is used and subjected to a heating treatment, danger of contamination of hepatitis virus and AIDS virus can be avoided. The heat treatment which is commonly used for inactivation of virus may be used to treat plasma for use in preparing the immunoglobulin. For example, a liquid phase heat treatment at 60° C. for 10 hours, an evaporating heat treatment at 60° C. for 10 hours, a drying heat treatment at 65° C. for 96 hours, etc. are usually conducted for fractionated plasma preparations and may be used to heat treat the immunoglobulin or its source herein.

In the case of application to animals other than human beings, immunoglobulin may be prepared from an animal other than a human being depending upon the type of the animal to be treated. For example, if a mouse is to be treated, mouse immunoglobulin may be prepared.

Immunoglobulin has various classes such as IgG, IgA, IgM, etc. For the immunoglobulin of the present invention, each class or type of immunoglobulin may be employed either solely or jointly together. In embodiments of the invention, the immunoglobulin which is employed may be a commercially available animal or human γ-globulin fraction of serum proteins, or one or more purified immunoglobulins such as animal or human IgG, IgA, or IgM which are disclosed, for example, in the 1995 Sigma Chemical Co. Catalog of "Biochemical Organic Compounds for Research and Diagnostic Reagents," Sigma Chemical Company, St. Louis, Mo., pp 470–472, and 1365–1368 (1995), herein incorporated by reference.

Free histamine and its pharmaceutically acceptable salts such as hydrochloride, phosphate and picrate salts, may be used alone or in combination as a histamine component.

In the manufacture of the drug preparation for oral administration of the present invention, it can be prepared, for example, by dissolving about 1 mg to about 200 mg, preferably about 5 mg to about 50 mg, of immunoglobulin and about 0.01 $\mu$g to about 2 $\mu$g, preferably about 0.05 $\mu$g to about 0.5 $\mu$g, of a histamine component in a suitable pharmaceutically acceptable solution such as physiological saline solution, distilled water, etc. with conventional means, mixing and stirring. The histamine-added immunoglobulin may be stored in frozen or freeze-dried form.

The histamine-added inimunoglobulin of the present invention can be used either solely or jointly together in pharmaceutically effective amounts with pharmaceutically effective amounts of other pharmaceutically-active components for treating animals or humans.

The preparations for oral administration of the present invention may contain histamine-added immunoglobulin as an effective component, alone or together with commonly-used pharmaceutically acceptable excipients in pharmaceutically acceptable amounts such as a suitable pharmaceutically acceptable additive or carrier (e.g. lactose, mannitol, corn starch, potato starch, calcium citrate, etc.) mixed with one or more pharmaceutically acceptable: (1) binders such as crystalline cellulose, cellulose derivatives (e.g. hydroxypropylcellulose), gum arabicum, corn starch, gelatin, etc., (2) disintegrating agents such as corn starch, potato starch, carboxymethylcellulose, etc., (3) lubricating agents such as talc, magnesium stearate, etc., and (4) other pharmaceutically acceptable excipients including pharmaceutically acceptable bulking agents, moisturizing agents, buffers, preservatives, perfumes and the like to obtain tablets, diluted powders, granules or capsules.

Furthermore, in embodiments of the invention, the histamine-added immunoglobulin of the present invention may be prepared as an orally administrable solution dissolved into distilled water etc. upon actual use. Thus, the solution of histamine-added immunoglobulin may be prepared in a dry state or a solution may be filled in vials or the like followed by freeze-drying. In the manufacture of this preparation, if necessary, the above mentioned additives or carriers may be added in pharmaceutically acceptable amounts.

The preferred dose of a preparation of histamine-added immunoglobulin is once or twice a week by a hypodermic injection of one vial containing 12 mg of human immunoglobulin and 0.15 $\mu$g of histamine hydrochloride per vial, and it is allowed to increase to 3 vials, as written in said "Drugs in Japan, Ethical Drugs," edited by Japan Pharmaceutical Information Center; published by Yakugyo Jiho Co., Ltd., Japan, pp. 463–464 (October 1996). According to the following pharmacological tests, the drug preparation for oral administration of the present invention shows almost the same pharmaceutical activity as a hypodermic injection of the histamine-added immunoglobulin in the same dose. However, a preparation for oral administration is usually needed in a higher dose than a hypodermic injection to achieve the same efficacy. Therefore, the preferred dose of the preparation of the present invention may vary depending upon the type of the disease, the condition of the patient, age or sex of the patient, form of the preparation, method for the administration, term for the administration, etc. To achieve a desired effect, 1–300 mg, preferably 5–150 mg may be usually administered to common adults once or several times a week.

The method of manufacturing the histamine-added immunoglobulin of the present invention, and its pharmaceutical activity and stability, will be further illustrated by way of the following example wherein all parts, percentages, amounts, and ratios are by weight, all pressures are atmospheric, and all temperatures are room temperature and in ° C., unless otherwise indicated:

EXAMPLE

In this example, the preparation of orally administrable histamine-added immunoglobulin of the present invention and its pharmacological activity and stability is illustrated. Mice were used as experimental animals in the following pharmacological tests and, accordingly, mouse immunoglobulin was used in place of human immunoglobulin. Both types of histamine-added immunoglobulin may be produced in the same manner. Thus, for the pharmacological tests on mice, a mouse immunoglobulin and histamine dihydrochloride were dissolved in physiological saline solution using the following mixing ratios, stirred at room temperature for 2 hours, freeze-dried and upon use, dissolved by adding a physiological saline solution thereto for oral administration:

| Product of the present invention | Amount of mouse immunoglobulin | Amount of histamine.2HCl |
|---|---|---|
| HG50 | 5.3 mg | 0.10 $\mu$g |
| HG75 | 12.0 mg | 0.15 $\mu$g |
| HG90 | 28.8 mg | 0.30 $\mu$g |

Each of the HG50, HG75 and HG90 products prepared above exhibited significant effects in all of the following pharmacological tests and, accordingly, only the results obtained for HG75 are given as representative thereof.

I. IMMUNOMODULATING ACTION

The immunomodulating action was measured using production of antibody specific to trinitrophenyl (TNP) as a target.

(1) Preparation of Trinitrophenyl-Bonded Sheep Red Blood Cells (TNP-SRBC)

Trinitrobenzenesulfonic acid (TNBS) was dissolved in a physiological saline solution buffered with phosphoric acid to prepare a solution (40 mg/7.0 ml; pH 7.2) and then 1 ml of sheep red blood cell pellets was dropped thereinto with stirring. The mixture was allowed to stand at room temperature with frequent stirring under a light-shielding state and washed with a physiological saline solution three times. Then it was centrifuged at 3,000 rpm for 5 minutes and converted into a solution of $5 \times 10^9$ cells/ml using a physiological saline solution.

(2) Production of a TNP-Specific Antibody

TNP-SRBC ($10^9$ cells) was intraperitoneally administered to male BALB/c mice having an age of 6 to 8 weeks. The anti-TNP antibody in their serum was measured by an enzymatic immunoassay (ELISA) using a dinitrophenyl-bovine serum albumin (DNP-BSA). The result was that a potent antibody production of anti-TNP-IgM and anti-TNP-IgG was noted having a peak on the 4th to 6th days. In the case of BALB/c nude mice having no thymus, production of antibodies of both types was rarely noted.

(3) Measurement of the Action of the Tested Drugs

The above-mentioned test system was used for checking the actions of histamine-added mouse immunoglobulin of the present invention (150 mg/kg/day) to the anti-TNP antibody production by oral administration for 4 days from the sensitization with TNP-SRBC. Also, the actions of histamine-added mouse immumunoglobulin (150 mg/kg/day) by a hypodermic injection was checked as a positive control in the same manner.

The result for the anti-TNP antibody production system is given in FIG. 1. In the test results, significant difference in the average values from the control was calculated by means of the Student's t-test and is expressed with asterisks (*:$p<0.05$, :$p<0.01$, *:$p<0.001$).

INHIBITORY ACTION TO HYPEREOSINOPHILICITY

Inhibitory action to hypereosinophilicity was evaluated for the histamine-added mouse immunoglobulin of the present invention which was administered orally, and for a positive control of histamine-added mouse immunoglobulin which was administered by injection using a hypereosinophilic model induced by ragweed pollen antigen:

(1) Hypereosinophilic Model Induced by Ragweed Pollen Antigen

In accordance with the method of Kaneko et al. (Int. Archs Allergy Appl. Immunol., 96, 41–45 (1991)), a ragweed pollen extract (which was diluted to an extent of 1,000 times using a physiological saline solution) was hypodermically injected into female BALB/c mice six to eight weeks old for sensitization at a dosage of 0.1 ml on the initiation day and on the first day, and 0.2 ml on the sixth, eighth and fourteenth days. On the twentieth day, 0.2 ml of a 1,000 times diluted ragweed antigen was intraperitoneally injected into the mice to induce reaction. On the 24th hour after the induction or injection, the peritoneal exudate cells were recovered and subjected to a Giemsa staining and the total cell numbers, number of eosinophils, number of neutrophils and number of mononuclear cells were counted. As a result, the numbers of the eosinophils peaked 24 hours after the induction. In the case of BALB/c nude mice having no T cells, no exudation to peritoneum was noted at all both in eosinophils and in neutrophils.

(2) Measurement of the Action of the Tested Drugs

Figure 2:
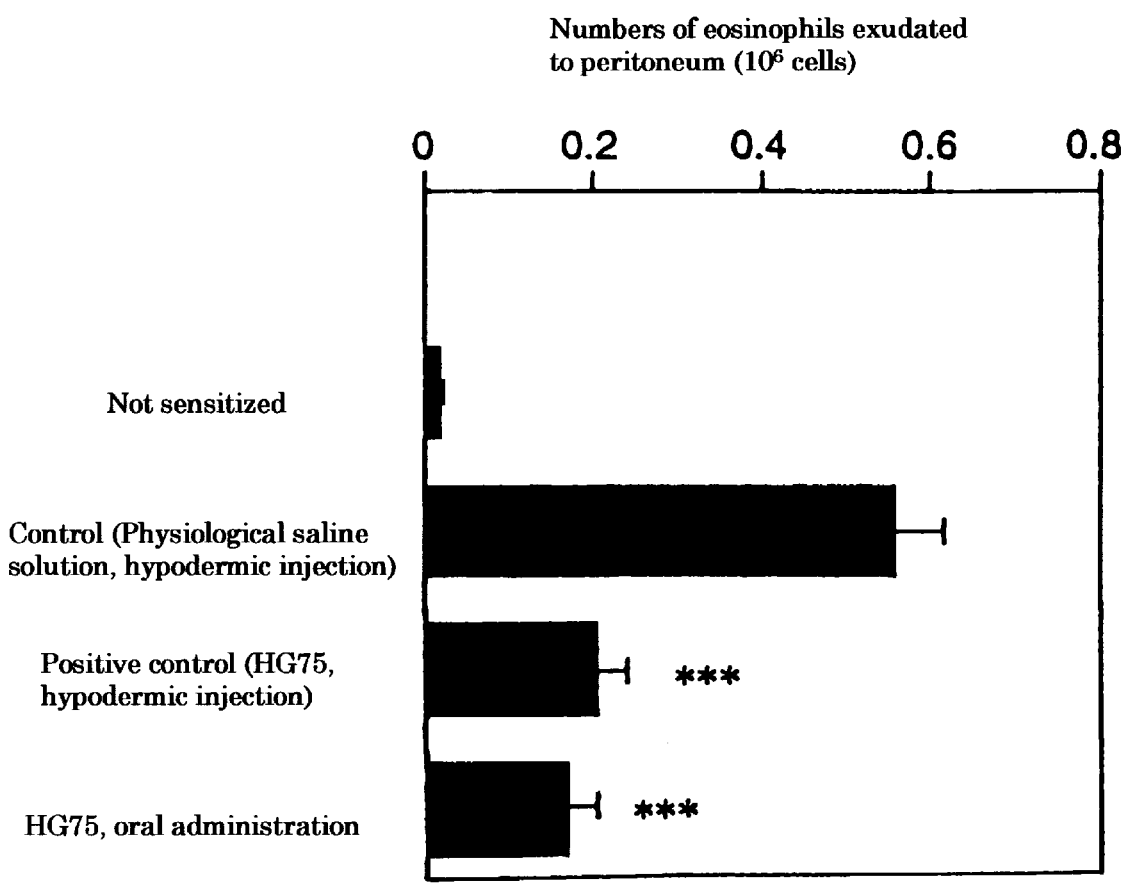
FIG. 2 is a graph showing the inhibitory action of a drug preparation of the present invention on hypereosinophilic models induced by ragweed pollen antigen.

The above mentioned hypereosinophilic models were used to check action towards the hypereosinophilicity by oral administration of histamine-added mouse immunoglobulin of the present invention (150 mg/kg/day) twice a week (on the initial day, on the fourth, seventh, eleventh, fourteenth and eighteenth days). Also, the action of histamine-added mouse immunoglobulin (100 mg/kg/day) by a hypodermic injection was checked as a positive control in the same manner. An example of the results is given in FIG. 2.

THE TEST FOR STABILITY

Figure 3:
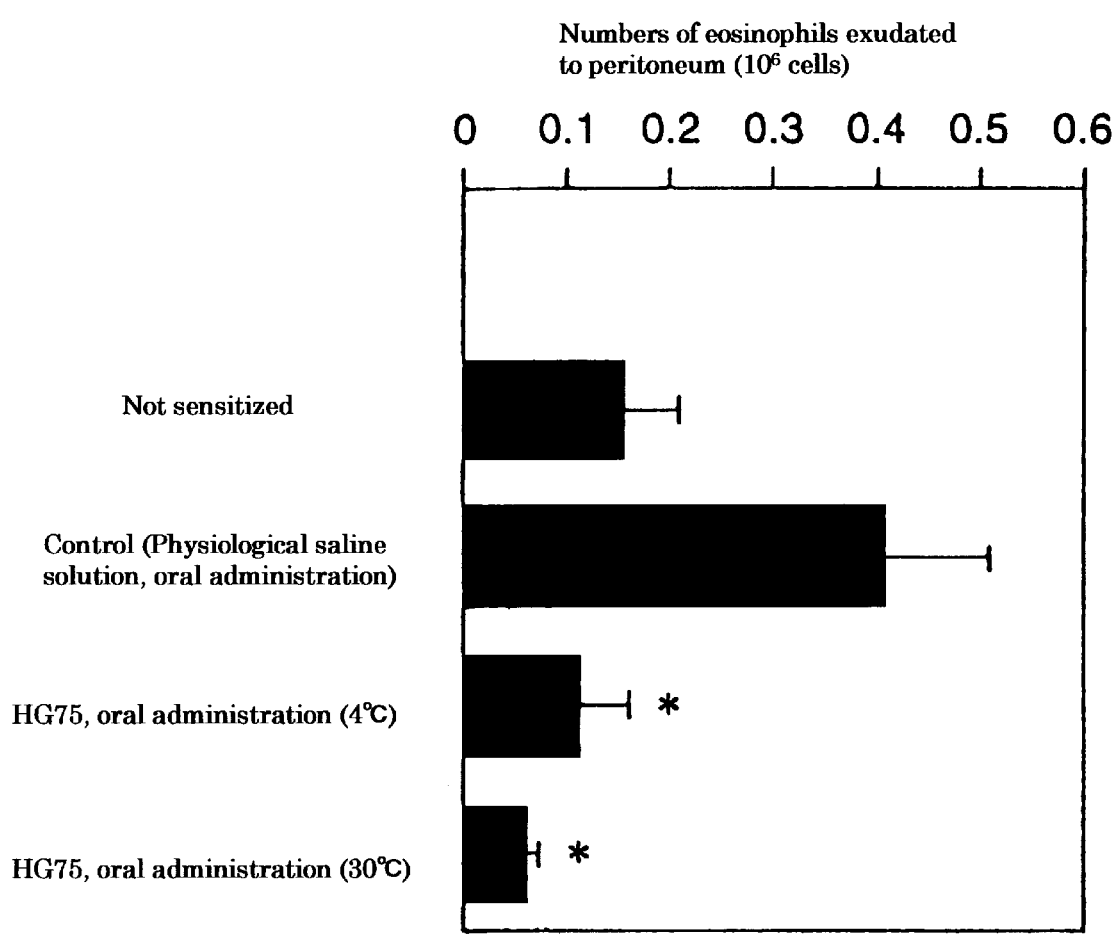
FIG. 3 is a graph showing the inhibitory action of drug preparations of the present invention stored for 6 weeks at 4° C. or 30° C. on hypereosinophilic models induced by ragweed pollen antigen.

A freeze-dried preparation of histamine-added mouse immunoglobulin of the present invention was stored for 6 weeks at 4° C. or 30° C. After the storage, each of the preparations was tested using the same procedure of said pharmacological test II above (inhibitory action to hypereosinophilicity) to check the stability of the preparation of the present invention. An example of the results is given in FIG. 3.

As shown in FIG. 1, orally administered histamine-added immunoglobulin of the present invention showed remarkable promoting actions to IgM and IgG antibody productions. It is also apparent from the results shown in FIG. 2 that the orally administered histamine-added immunoglobulin of the present invention significantly inhibited the eosinophil exudation into peritoneum in the hypereosinophilic models induced by ragweed pollen antigen. On the contrary, said pharmaceutical actions are not observed by the oral administration of each of the histamine component and immunoglobulin component.

Accordingly, the drug preparation for oral administration is useful as a pharmaceutical agent for prevention or treatment of various diseases on which the usual hypodermic injection has shown its pharmaceutical actions. Exemplary of such diseases which may be treated by the oral administration of the histamine-added immunoglobulin are allergic diseases such as bronchial asthma, allergic rhinitis, vasomotor rhinitis, urticaria, chronic eczema and atopic dermatitis; autoimmune diseases such as multiple sclerosis, chronic rheumatoid arthritis and systemic lupus erythematodes; various immunodeficiency syndromes; and also eosinophilia or various inflammatory diseases caused by infectious diseases, parasitic diseases, diseases of respiratory organs, autoimmune diseases, malignant tumors, etc. A drug preparation which can be administered orally, like the preparation of the present invention, can be taken by the patients easier than an injectable preparation. Therefore, the drug preparation for oral administration of the present invention is practical and highly useful.

We claim:

1. A method for the treatment of an allergic disease, autoimmune disease, immunodeficiency syndrome, inflammatory disease, or eosinophilia comprising orally administering to a patient in need of such treatment an orally ingestible, pharmaceutical composition comprising a pharmaceutically effective amount of a histamine-added immunoglobulin and a pharmaceutically acceptable carrier.

2. A pharmaceutical composition for oral administration comprising histamine-added immunoglobulin as an effective component and a pharmaceutically acceptable carrier, said histamine-added immunoglobulin being obtained by admixing an immunoglobulin component and a histamine component in a weight ratio of about 1 mg to about 200 mg of the immunoglobulin component to about 0.01 $\mu$g to about 2 $\mu$g of the histamine component, said pharmaceutical composition being in the form of a tablet, or capsule.

3. A pharmaceutical composition as claimed in claim 2 wherein said carrier is at least one member selected from the group consisting of lactose, mannitol, corn starch, potato starch, and calcium citrate.

4. A pharmaceutical composition as claimed in claim 3 further including at least one pharmaceutically acceptable member selected from the group consisting of pharmaceutically acceptable binders, disintegrating agents, lubricating agents, bulking agents, moisturizing agents, buffers, preservatives, and perfumes.

5. A pharmaceutical composition for oral administration according to claim 2, which is a therapeutic agent for allergic disease, autoimmune disease, eosinophilia suppression, or inflammation, said immunoglobulin being human immunoglobulin.

6. A pharmaceutical composition as claimed in claim 2, wherein said histamine-added immunoglobulin is obtained by admixing the immunoglobulin component and the histamine component in a weight ratio of about 5 mg to about 50 mg of the immunoglobulin component to about 0.05 $\mu$g to about 0.5 $\mu$g of the histamine component.

7. A pharmaceutical composition as claimed in claim 2, wherein the weight ratio between said histamine component and said immunoglobulin component is less than about $1.9 \times 10^{-5}$ g of the histamine component per 1 g of the immunoglobulin component.

8. A pharmaceutical composition as claimed in claim 2 wherein said histamine component is at least one pharmaceutically acceptable histamine salt.

9. A pharmaceutical composition as claimed in claim 8 wherein said salt is histamine dihydrochloride.

10. A pharmaceutical composition as claimed in claim 2 wherein said histamine-added immunoglobulin is formulated as a tablet.

11. A pharmaceutical composition for oral administration consisting essentially of histamine-added immunoglobulin as an effective component and a pharmaceutically acceptable carrier, said histamine-added immunoglobulin being obtained by admixing an immunoglobulin component and a histamine component in a weight ratio of about 1 mg to about 200 mg of the immunoglobulin component to about 0.01 $\mu$g to about 2 $\mu$g of the histamine component, said pharmaceutical composition being in the form of a tablet, or capsule.

12. A pharmaceutical composition as claimed in claim 11 wherein said carrier is at least one member selected from the group consisting of lactose, mannitol, corn starch, potato starch, and calcium citrate.

13. A pharmaceutical composition as claimed in claim 12 further including at least one pharmaceutically acceptable member selected from the group consisting of pharmaceutically acceptable binders, disintegrating agents, lubricating agents, bulking agents, moisturizing agents, buffers, preservatives, and perfumes.

14. A pharmaceutical composition for oral administration according to claim 11, which is a therapeutic agent for allergic disease, autoimmune disease, eosinophilia suppression, or inflammation, said immunoglobulin being human immunoglobulin.

15. A pharmaceutical composition as claimed in claim 11, wherein said histamine-added immunoglobulin is obtained by admixing the immunoglobulin component and the histamine component in a weight ratio of about 5 mg to about 50 mg of the immunoglobulin component to about 0.05 $\mu$g to about 0.5 $\mu$g of the histamine component.

16. A pharmaceutical composition as claimed in claim 11, wherein the weight ratio between said histamine component and said immunoglobulin component is less than about $1.9 \times 10^{-5}$ g of the histamine component per 1 g of the immunoglobulin component.

17. A pharmaceutical composition as claimed in claim 11 wherein said histamine component is at least one pharmaceutically acceptable histamine salt.

18. A pharmaceutical composition as claimed in claim 17 wherein said salt is histamine dihydrochloride.

19. A pharmaceutical composition as claimed in claim 11 wherein said histamine-added immunoglobulin is formulated as a tablet.

20. A pharmaceutical composition as claimed in claim 11 wherein said immunoglobulin is IgG.

* * * * *